US008073713B2

(12) United States Patent
Thorne et al.

(10) Patent No.: US 8,073,713 B2
(45) Date of Patent: Dec. 6, 2011

(54) METHOD AND SYSTEM FOR MANAGING MEDICAL PROFESSIONALS

(75) Inventors: Curtis J. Thorne, Nashville, TN (US); Gregg Phillip Allen, Franklin, TN (US)

(73) Assignee: Premerus, LLC, Franklin, TN (US)

( * ) Notice: Subject to any disclaimer, the term of this patent is extended or adjusted under 35 U.S.C. 154(b) by 358 days.

(21) Appl. No.: 12/365,796

(22) Filed: Feb. 4, 2009

(65) Prior Publication Data
US 2009/0204436 A1 Aug. 13, 2009

Related U.S. Application Data

(60) Provisional application No. 61/065,055, filed on Feb. 8, 2008, provisional application No. 61/065,062, filed on Feb. 8, 2008, provisional application No. 61/065,085, filed on Feb. 8, 2008, provisional application No. 61/065,061, filed on Feb. 8, 2008.

(51) Int. Cl.
*G06Q 10/00* (2006.01)
(52) U.S. Cl. ............... 705/3; 705/2
(58) Field of Classification Search ............ 705/2, 3
See application file for complete search history.

(56) References Cited

U.S. PATENT DOCUMENTS

| | | | |
|---|---|---|---|
| 7,831,445 B2* | 11/2010 | Reiner | 705/2 |
| 2002/0010395 A1* | 1/2002 | Strawder | 600/407 |
| 2005/0018787 A1 | 8/2005 | Tomlinson, Jr. et al. | |
| 2005/0256743 A1 | 11/2005 | Dale | |
| 2006/0122865 A1 | 1/2006 | Preiss et al. | |
| 2006/0106640 A1 | 5/2006 | Deline | |
| 2006/0173663 A1 | 8/2006 | Langheier et al. | |
| 2007/0011024 A1 | 1/2007 | Dale et al. | |
| 2007/0136355 A1 | 6/2007 | Haider | |
| 2007/0232868 A1* | 10/2007 | Reiner | 600/300 |
| 2007/0250352 A1 | 10/2007 | Tawil | |
| 2008/0004904 A1 | 1/2008 | Tran | |
| 2008/0306760 A1* | 12/2008 | Minnigh et al. | 705/2 |
| 2009/0094058 A1* | 4/2009 | Reiner | 705/3 |

FOREIGN PATENT DOCUMENTS

| | | |
|---|---|---|
| WO | WO2006057953 | 1/2006 |
| WO | WO2007062523 | 7/2007 |
| WO | WO 2007089686 A2 * | 8/2007 |

OTHER PUBLICATIONS

Woodward et al, "Performance assessment for radiologists interpreting screening mammography," Jul. 17, 2006, Wiley InterScience, 26: 1532-1551.*
Non-Final Rejection mailed Jun. 6, 2011 for U.S. Appl. No. 12/365,787.

* cited by examiner

*Primary Examiner* — Lena Najarian
(74) *Attorney, Agent, or Firm* — SNR Denton US LLP (57) ABSTRACT

A system and method for improving medical care through tracking reported findings or diagnoses of patient medical conditions and feeding back actual medical conditions and patient medical condition outcomes to determine accuracy of the reported findings. By feeding back the actual medical conditions and patient medical condition outcomes, a quantitative measure of each reported finding of each medical professional can be determined. One medical professional expertise in which the feedback system can be particularly useful is with medical image reading professionals, as this medical professional expertise provides a basis for other medical professionals to determine treatment and/or additional testing options.

6 Claims, 7 Drawing Sheets

METHOD AND SYSTEM FOR MANAGING MEDICAL PROFESSIONALS

CROSS-REFERENCE TO RELATED APPLICATIONS

This application claims priority to the following U.S. Provisional Patent Applications: Ser. No. 61/065,055 filed on Feb. 8, 2008; 61/065,062 filed on Feb. 8, 2008; 61/065,085 filed on Feb. 8, 2008; and 61/065,061 filed on Feb. 8, 2008, the entire teachings of which are herein incorporated by reference.

BACKGROUND

The practice of medicine has greatly advanced as evidenced by patients being treated with previously incurable diseases, such as cancer. One reason, among many, for the advancement of medicine is a result of improvement of medical imaging technology. Medical images may include many different types of images of the human body, including radiological images, CAT scan images, endoscopic images, magnetic resonance images, etc. Through the use of medical imaging technology, medical professionals are able to see images of internal organs, for example, of patients to help diagnose medical conditions of the patients. Medical imaging allows for diseases, such as breast cancer, to be diagnosed in early stages, which greatly improves chances of recovery. While medical imaging technology has significantly improved medical care, because of the nature of creating and interpreting medical images, radiological or other imaging techniques, inaccuracies in the imaging and interpretation processes of the medical images may result. Because of the inaccuracies in the imaging and interpretation processes, patient medical conditions are often misdiagnosed.

Misdiagnosis of a medical condition, such as a disease, may come in the form of false positives, false negatives, and equivocal diagnoses. A false positive is a detection of a disease that does not exist. A false negative is a failure to detect a disease that is present in a patient. An equivocal diagnosis is a statement that a definitive diagnosis cannot be made based on the information available (e.g., "cancer cannot be ruled out"). Each of these misdiagnoses results in higher costs of treatment, additional suffering to patients, and additional burden on the healthcare system as a whole. It has been estimated by the American College of Radiology that frequency of misdiagnosis of radiological imaging interpretations is as high as 30%. And, given that it has been estimated that 40% to 60% of total healthcare spend is influenced by radiological imaging and interpretations therefrom, misdiagnoses results from misinterpretation of medical imaging has a large impact on the healthcare system.

An example of the effects of a misdiagnosis is as follows. A medical image reading professional identifies a spot on a lung. The lung spot may be any of a number of different medical conditions, including a benign solitary pulmonary nodule, small cell lung carcinoma, non-small cell lung carcinoma, or any number of other medical conditions. If the medical image reading professional determines that the lung spot is a benign solitary pulmonary nodule, but also denotes that "cancer cannot be ruled out," a treating medical professional is compelled to perform additional testing, a biopsy of the lung spot, and possibly surgery to remove the lung spot, to avoid a malpractice claim. The cost for each of these additional diagnostic treatments can be very high from financial, patient anxiety and pain, and medical system resource perspectives. If it turns out that after the additional diagnostic treatments that the patient had a benign, solitary pulmonary nodule that could have been identified by the medical image reading professional at the initial medial image reading, all of the additional diagnostic treatments would have been avoided.

Although medical professionals are considered to be highly regarded, and justifiably so in most cases, medical professionals are not all trained in the same manner or have the same level of proficiency as one another. As in all professions, some medical professionals may have better education, training, or any other differentiator than other medical professionals. For example, one medical image reading professional may have better eyesight or cognitive reasoning skills than another and, therefore, be better at determining a correct or more accurate diagnosis than another with worse eyesight or cognitive reasoning skills. One problem that is a dilemma for the healthcare system is that absent clear cases of malpractice that result in the unfortunate injury or death of a patient, it is difficult to quantitatively determine proficiency of medical professionals given the vast number of medical professionals in the healthcare system.

SUMMARY

To overcome the problems of burden on the healthcare system due to misdiagnoses and not being able to quantitatively determine proficiency of medical professionals, the principles of the present invention provide for improving medical care through tracking reported findings or diagnoses of patient medical conditions and feeding back actual medical conditions and patient medical condition outcomes to determine accuracy of the reported findings. By feeding back the actual medical conditions and patient medical condition outcomes, a quantitative measure of each reported finding of each medical professional can be determined. One medical professional specialty in which the feedback system can be particularly useful is with medical image reading professionals, as this medical professional specialty provides a basis for other medical professionals to determine treatment and/or additional testing options.

One embodiment of a process for managing a network of medical professionals may include collecting information associated with patients of medical professionals in a network of medical professionals. The patient information may include clinical condition information. Reported findings of a clinical condition of each patient by a medical professional may be monitored. A determination may be made as to whether the reported findings of the clinical condition of each patient by the medical professional is accurate compared to actual clinical condition of each respective patient. A score may be generated for each reported finding by the medical professional, where the score may be indicative of accuracy of each reported finding as compared to the actual clinical condition of the patient. A summary score may be calculated using the scores for the medical professional. Based on the summary score of the medical professional, a determination may be made as to whether the medical professional is to remain in the network of medical professionals.

Another process for improving medical care may include providing medical condition information of anatomical regions of patients to first medical professionals for interpreting the medical condition information to describe medical conditions of the respective patients. The interpretations of the medical condition information may be provided to second medical professionals to treat the respective patients for medical conditions described in the interpretations by the first medical professionals. In one embodiment, the first medical professionals may be medical image reading professionals and the second medical professionals may be treating medical professionals, such as treating physicians. Patient outcome information associated with outcome of the patients treated for the medical conditions described in the interpretations may be collected. The outcome information may include information collected from medical insurance claims, treatment reports, and random quality assurance medical image readings. The collected patient outcome information may be stored in association with information of respective first medical professionals who interpreted medical condition information of the respective patients. A determination may be made as to an overall competency metric for each first medical professional indicative of performance of each respective first medical professional based on the collected patient outcome information. A determination may be made as to whether each first medical professional is to be provided medical condition information of other patients based on respective overall competency metrics. In other words, if a medical professional, such as a medical image reading professional, is determined to be highly competent (e.g., 98% or above), then the medical professional may continue to be provided with work (e.g., reading additional medical images of patients). However, if a medical professional, such as a medical image reading professional, is determined to be less than highly competent (e.g., 95% or below), then work may be discontinued from being delivered to the medical professional or the medical professional may be terminated from the medical professional network.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF DRAWINGS

Figure 1:
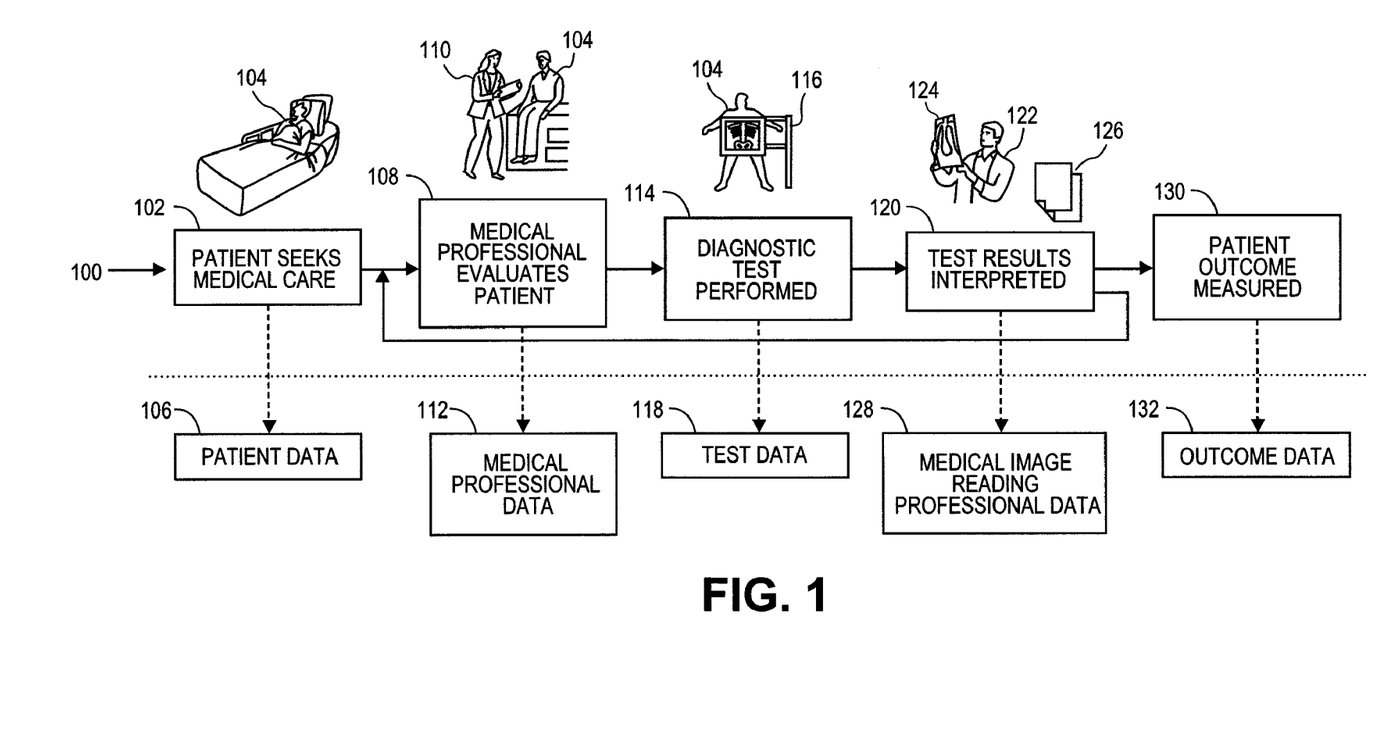
FIG. 1 is a flow chart of an exemplary process for treating a patient with a medical condition.

FIG. 1 is a flow chart of an exemplary process 100 for treating a patient with a medical condition. The process 100 starts at step 102, where the patient 104 seeks medical care. When the patient 104 seeks medical care, patient data 106 may be collected. The patient data 106 may include patient demographics, physical characteristics, and medical condition symptoms. The patient demographics may include age, gender, race, address, occupation, or other demographics that describe the patient 104. The patient physical parameters may include height, weight, body mass index, physical deformities or handicap, or any other physical attribute that describes the patient 104. The medical condition symptom information may include any information that the patient 104 can provide that describes the medical condition of the patient or that a medical professional can identify visually or through the use of medical equipment from the patient 104. The patient data may be collected and stored in a data repository, such as a database, for later use in determining proficiency of one or more medical professionals in diagnosing the patient's medical condition.

At step 108, a medical professional 110 evaluates a patient 104. The medical professional 110 may be a primary care physician, specialist, or any other medical professional who evaluates patients having medical conditions. In evaluating the patient 104, the medical professional 110 may review the patient data 106 that includes symptoms of the medical condition of the patient. The medical professional 110 may further examine the patient 104 to diagnose the medical condition of the patient 104. The evaluation may result in the medical professional 110 being able to request one or more diagnostic tests to be performed on the patient 104 to better assess the medical condition of the patient 104.

Medical professional data 112 may be collected for use in determining competency of the medical professional 110. The medical professional data 112 may include demographics, including medical specialty or expertise, medical subspecialty or expertise, age, years in practice, location of practice, practice affiliation to institutions or groups, address, and any other demographic of the medical professional 110 that may be useful in determining qualifications and experience of the medical professional 110. While the medical professional data 112 may provide an indication as to the qualifications and competency of the medical professional 110, the medical professional data 112 may be a starting point for determining competency as patient results is the ultimate indicator of competency for a medical image reading professional. Furthermore, the medical professional data 112 may include initial diagnosis of the patient 104, clinical question(s) asked by medical professional 110 in diagnosing the patient 104, and diagnostic test(s) to be performed on the patient 104 as requested by the medical professional 110 to further determine the medical condition of the patient 104.

At step 114, a diagnostic test requested by the medical professional 110 may be performed on the patient 104. The diagnostic test may be one that involves medical imaging using a medical imaging machine 116. It should be understood that the medical imaging may be any imaging utilized in attempting to diagnose a medical condition of the patient 104.

Diagnostic test data 118 may be collected. The diagnostic test data 118 may include demographics about the testing facility, demographics on the medical professionals performing the tests, identification of the test that was performed, survey results of the testing facility and testing medical professional, and any other data that may be helpful in ascertaining performance of the testing facility or testing medical professionals. The demographics of the testing facility may include the facility identity, testing modalities offered at the facility, equipment brand, equipment model, equipment type, software version, or any other information associated with the equipment, physical location, and any other information about the testing facility that may be relevant in determining the quality of the facility and the medical professionals who work at the facility. The demographics of the testing medical professionals may include identity, training, education, gender, years of experience, acceptability of tests for interpretation, and any other demographic information associated with the testing medical professional.

At step 120, medical test results may be interpreted by a medical professional 122. In one embodiment, the medical professional 122 is a medical image reading professional, such as a radiologist, who specializes in reading medical images 124. In reading the medical images 124, the medical professional 122 may create a report 126 or clinical finding from the medical images 124. In one embodiment, the medical images 124 include a set of medical images, where the set of images 124 may include one or more medical images from one or more different medical imaging machines.

Medical image reading professional data 128 may be collected about the medical professional 122 who is performing the interpretation, findings, or diagnosis of the medical tests. The medical image reading professional data 128 may include demographics of the medical image reading professional, operational or experience information of the medical image reading professional 122, and survey results of the medical image reading professional 122 by the patient 104 or medical professional 110. The demographics of the medical image reading professional 122 may include certifications, years of practice, education, training, or any other demographic information associated with the medical image reading professional. Operational information of the medical image reading professional may include volume of studies performed over a period of time (e.g., monthly), accuracy of diagnoses, which may be developed over time, and equivocal ratio (e.g., number of studies performed in which the medical image reading professional 122 equivocates in the diagnoses versus the total number of studies performed over a time period (e.g., monthly or yearly)). The survey results may be provided by the patient 104 or the medical professional 110. The report 126, which includes a diagnosis or clinical finding of the patient 104, may be provided back to the medical professional 110 at step 108 for the medical professional 110 to further diagnosis and treat the patient 104 based on, at least in part, the report 126 of the medical condition of the patient 104. It is at this phase where a correct or incorrect interpretation of medical test results affect treatment plans by the medical professional 110. If the interpretation of the medical tests (e.g., radiological image) is incorrect, then the medical professional 110 is likely to generate a treatment plan for the patient 104 based on an incorrect interpretation of the medical test.

At step 130, the patient outcome may be measured. It should be understood that step 130 may be measured after each time the test results are interpreted at step 120 or after any other step in the process 120 if the process 100 loops back to step 108 without having to pass through each of steps 108, 114, and 120. Outcome data 132 may be generated based on health care claim records, treatment reports of clinical results from follow-up care, and patient survey results. It should be understood that these outcome data points are exemplary and that alternative and/or additional outcome data may be generated. The healthcare claim records may be any claim records submitted for an episode of care, where an episode of care is defined as medical care that is provided to a patient for test and treatment of a medical condition, which may include co-morbid conditions (e.g., amputations), as understood in the art. For example, if the patient has chest pains, then the episode of care may include any medical treatment associated with treating the patient's chest pain. Medical treatment may include diagnostic tests, such as images, radiological, MRI, or otherwise, that are performed one time or multiple, iterative diagnostic tests as a result of diagnoses, correct or incorrect, of the patient. The episode of care may be considered complete once the actual medical condition is determined and the patient is provided with a treatment plan that cures the actual medical condition. It should be understood that the actual medical condition may take one or more diagnostic tests and treatment plans to be correctly identified. Should the medical condition persist, so does the episode of care. The clinical results from follow-up care may be results determined by the medical professional 110 who determines whether the patient's medical condition as diagnosed improves and, thereby, is determined to be the actual medical condition. The patient's survey results may include a survey taken by a patient who assesses the performance of one or more medical professionals who are involved in diagnosing and treating the patient. Each of these outcome data may be utilized in generating a performance score for the medical image reading professional 122 and, optionally, medical professional 110.

Figure 2:
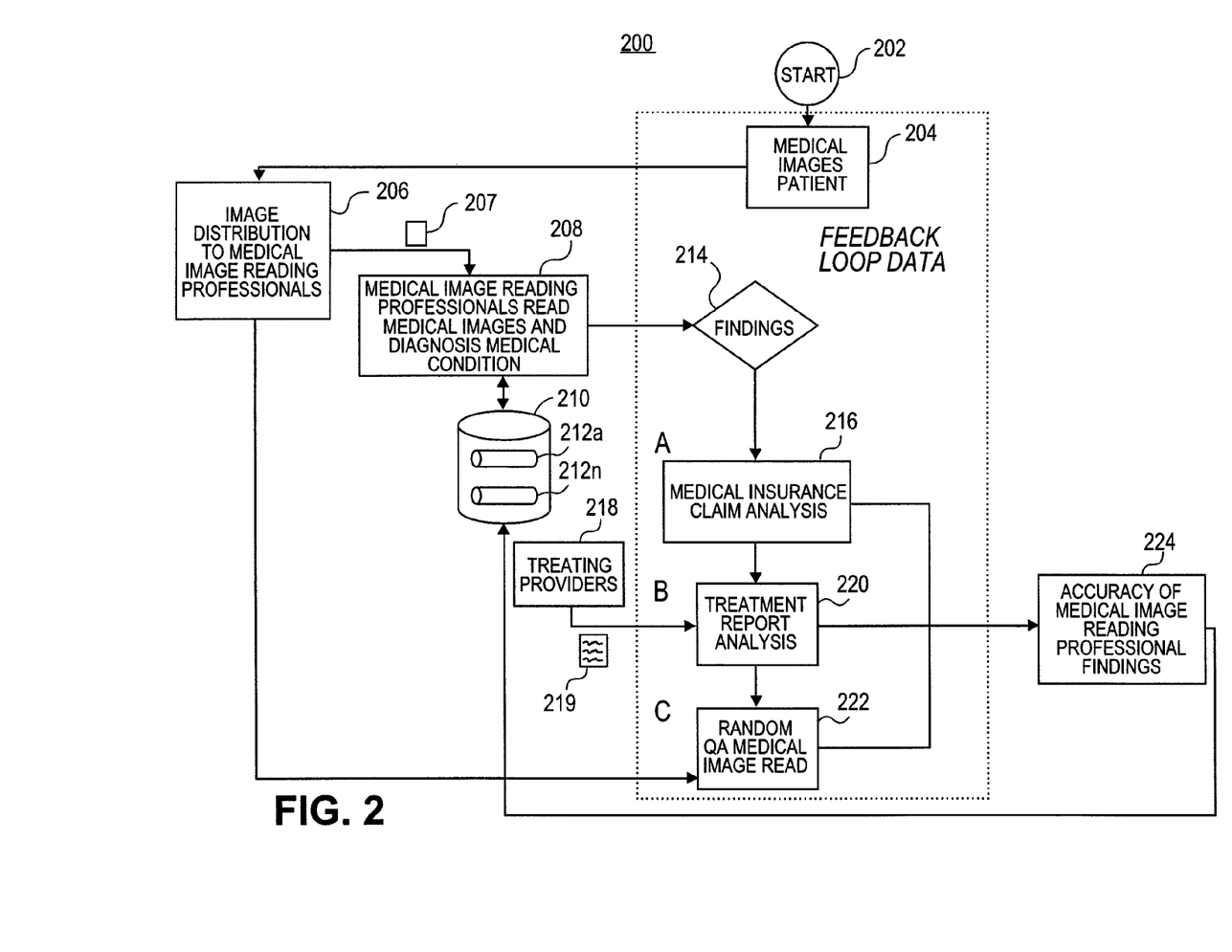
FIG. 2 is a flow diagram of an exemplary process for collecting medical information associated with diagnostic testing and treatment of patients and feeding back the information to determine proficiency of a medical image reading professional.

FIG. 2 is an exemplary flow diagram of an exemplary process 200 for collecting and feeding back medical information associated with patients for determining proficiency of medical professionals. The process 200 starts at step 202. At step 204, medical images of a patient may be collected. At step 206, distribution of the medical images to medical image reading professionals may be performed. In distributing the medical images 207, the medical images may be posted on a website, positioned in one or more queues, emailed, physically mailed, or otherwise distributed as understood in the art. At step 208, a medical image reading professional may read the medical images and make a diagnosis of a medical condition of the patient based on the medical images 207. A storage unit 210 may store data repositories 212a-212n (collectively 212) that may be configured to store the medical images 207 and findings of the medical image reading professional from reading the medical images 207. In one embodiment, the data repositories 212 are databases, relational or otherwise. In addition, patient data 106, medical professional data 112, test data 118, medical image reading professional data 128, and outcome data 132, as presented in FIG. 1, may be stored in the data repositories 212.

At step 214, clinical findings of the medical image reading professional from step 208 may be collected and used for performing a medical insurance claim analysis at step 216. The medical insurance claims may include, but are not limited to, evidence of continued eligibility of patients 102 in insurance plan(s), positron emission tomography (PET) insurance claims, biopsy insurance claims, surgery insurance claims, and chemotherapy insurance claims or the absence of medical claims indicative of the episode of care under evaluation in step 130. In collecting the medical insurance claims, claim codes indicative of diagnoses or treatments being performed may be collected and stored. The medical insurance claim analysis 216 may be performed by a medical image reading professional network manager or affiliate by accessing medical insurance claims associated with a patient of whom the medical images 207 were taken. The medical insurance claim analysis 216 may evaluate medical insurance claims to determine what medical treatment a treating physician commenced in response to a medical image reading professional diagnosing a medical condition of a patient. As previously described, an episode of care may include medical treatments and procedures performed on a patient in an attempt to treat a medical condition of a patient. Should a patient be misdiagnosed by a medical image reading professional, the episode of care for a single medical condition may extend beyond what is needed to treat the patient. The medical insurance claims may provide a "paper trail" for an episode of care, thereby enabling collection and analysis of the medical insurance claims to determine whether or not a medical image reading professional has correctly diagnosed or misdiagnosed a medical condition of a patient.

Treating providers or physicians 218 who are working with a patient to provide treatment or other diagnostic tests, including providing medical procedures, prescribing medical procedures, and providing medicines, generate treatment reports 219. At step 220, a treatment report analysis may be performed by a medical image reading professional network manager or affiliate to collect information and determine whether or not a patient outcome 130 for a medical condition diagnosed by the medical image reading professional confirms that the medical image reading professional provided a diagnosis that was accurate such that the treating provider was not mislead to create a treatment plan that was unwarranted. The treatment reports 219 may include, but are not limited to, PET reports, biopsy reports, clinical records, evaluation notes, metrics of disease progress/status, and surgical reports. In collecting the treatment reports, codes, words, or other information from the reports that are indicative of a patient's treatment plan may be collected and stored.

At step 222, a random quality assurance medical image read may be performed by a medical image reading professional to ensure quality of each medical image reading professional in a network of image reading professionals. In other words, medical images may be distributed to more than one medical image reading professional in a network of medical image reading professionals for quality assurance medical image reading professionals to compare diagnoses of medical conditions of a patient by each of the medical image reading professionals. The random quality assurance medical image readings may be performed on a certain percentage of all medical imaging, thereby being cost effective and providing a certain level of scrutiny to ensure that medical image reading professionals believe that they are to maintain a high level of intensity and quality. Statistical methods may be applied to evaluate the implications of differences or sameness for each of the medical image reading professionals related to their accuracy of their medical image reading professional clinical findings at step 224.

Results of the medical insurance claim analysis at step 216, treatment report analysis at step 220, and random quality assurance medical image reads at step 222 may be used at step 224 to determine accuracy of medical image reading professionals' clinical findings. Accuracy of the medical image reading professionals' clinical findings may be objective, subjective, or a combination thereof and determined by a software program, board of medical professional reviewers, or by any other means or mechanisms such that each medical image reading professional may have his or her accuracy of reading medical images reviewed, scored or graded. The accuracy of findings of a medical image reading professional may be fed back to be collected in the data repositories 212 and used for monitoring the medical image reading professional. In monitoring the medical image reading professional, scores or grades generated of each medical image reading professional may be stored and processed for analysis to determine overall accuracy of each medical image reading professional.

As understood in the art, there are different potential outcomes of diagnostic interpretations. TABLE I shows exemplary reported findings (columns) of medical conditions versus actual clinical conditions (rows) of the medical conditions. As shown, each reported finding of a medical image reading professional may be a finding of "negative," "positive," and "equivocal." Similarly, each actual clinical condition may be a medical condition of "negative," "positive," and "equivocal." Each of the cells defined by the rows and columns shows whether the medical image reading professional provided a diagnosis that was accurate, false positive, or false negative.

TABLE I

| | | Reported Finding | | |
| --- | --- | --- | --- | --- |
| | | Negative | Positive | Equivocal |
| Actual Clinical Condition | Negative | Accurate | False Positive | False Equivocal |
| | Positive | False Negative | Accurate | False Equivocal |
| | Equivocal | False Negative | False Positive | Accurate |

Each of the reported findings versus an actual clinical condition may be assigned a score. For example, if it is determined that the medical image reading professional is accurate in his or her diagnosis of a patient's medical condition then a score of zero may be assigned for that particular patient. If, however, a determination is made that the diagnosis by the medical image reading professional is a false positive, then a score of 75 may be assigned to the medical image reading professional for that patient. If the medical image reading professional diagnosis of a patient results in a false negative, then a score of 100 may be assigned to the medical image reading professional for the patient. If the medical image reading professional provides a diagnosis of a false equivocal, then a score of 50 may be assigned to the medical image reading professional for that patient. It should be understood that the scores may be applied such that the lower the score, the more proficient the medical image reading professional is performing. It should also be understood that scores, grades, or other metric may be assigned to each of the false positives, false negatives, false equivocals, and accurate diagnoses. It should also be understood that the scores may be assigned such that the higher the score (e.g., 100%), the more proficient the medical image reading professional is considered at performing diagnoses of medical conditions from medical images.

The scores developed of medical image reading professional producing accurate, false positive, false negative, or false equivocal readings may be included in a table or otherwise to produce a total, average, or other mathematically computed score of the medical image reading professional. TABLE II provides a listing of patients, diagnostic accuracies, and scores associated with each of the patients and diagnostic accuracies to produce an average score of the medical image reading professional. As shown, an accurate reading produces a score of zero while a false negative reading produces a score of 100. As previously described, the scores may be reversed, such that the more accurate the readings the higher the number on a basis of 100, for example.

TABLE II

Dr. AAAA
Brain MRI Specialist

| Patient ID | Diagnostic Accuracy | Score |
|---|---|---|
| Patient 1 | Accurate | 0 |
| Patient 3 | Accurate | 0 |
| Patient 4 | Accurate | 0 |
| Patient 5 | False positive | 75 |
| Patient 6 | False negative | 100 |
| Patient 7 | Accurate | 0 |
| Patient 8 | False Equivocal | 50 |
| Average | | 28.1 |

Each medical image reading professional may be included in a table to enable comparison of each of the medical image reading professionals. TABLE III shows an exemplary listing of medical image reading professionals and scores associated therewith. In one embodiment, the medical image reading professionals in the tables may be organized based on being the same expertise. For example, a table may include medical image reading professionals who are specialists in reading CT scans of hearts, lungs, brains, or any other anatomical region. Furthermore, if the medical image reading professionals are categorized as having a further level of expertise, such as reading CT scans of brains for a particular medical condition, such as cancer versus reading brains for head injuries, a table may be organized with the subspecialists. The table may be used for a variety of purposes. For example, the table may be used to sort the medical image reading professionals from best score to worse score, where any medical image reading professional having a score below a predetermined threshold, such as 80%, may be remediated or removed from a network of medical image reading professionals that perform readings of medical images of patients with particular medical conditions. The predetermined threshold may vary based on patient demographics, clinical question, modality, and anatomical region of patients.

TABLE III

Brain MRI Specialist MD Scores

| Physician ID | Score |
|---|---|
| Dr. AAAA | 28.5 |
| Dr. BBBB | 0 |
| Dr. DDDD | 1.4 |
| Dr. EEEE | 72.1 |
| Dr. FFFF | 12.8 |
| Dr. GGGG | 0 |
| Dr. HHHH | 51.6 |

Figure 3:
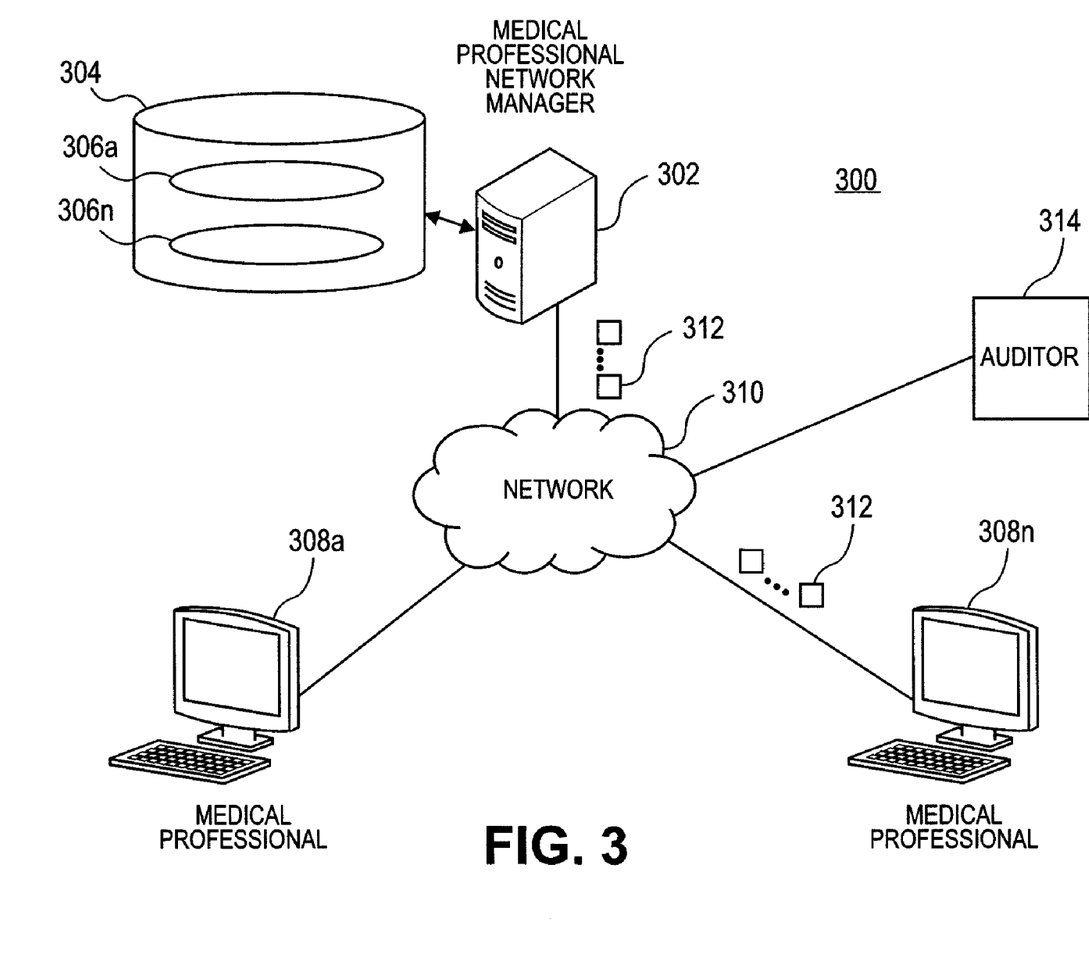
FIG. 3 is a block diagram of an exemplary network that enables a medical processional network manager to communicate with medical professionals to collect diagnostic and treatment information associated with patients and medical professionals in determining proficiency of the medical professionals.

FIG. 3 is a block diagram of an exemplary network 300 that enables a medical professional network manager to communicate with medical professionals to collect diagnostic and treatment information associated with patients and medical professionals in determining proficiency of the medical professionals. The system 300 may include a server 302 operated by a medical professional network manager. A storage unit 304, which may be part of or in communication with the server 302 may be configured to store data repositories 306a-306n (collectively 306) to store information provided in TABLE I-III and FIGS. 1 and 2.

The medical professional network manager may manage a network of medical image reading professionals who qualify to perform readings of medical images for specific anatomical regions (i.e., body part), conditions (e.g., disease or injury), and/or modalities (i.e., technology used for imaging).

Each of the groups of medical image reading professionals may utilize computing devices 308a-308n (collectively 308) to access information stored in the data repositories 306 via network 310. The medical image reading professionals may utilize the computing devices 308 to access a website or otherwise to download medical images associated with patients with medical conditions in which each medical professional specializes. For example, a medical professional who specializes in reading lungs or lung cancer may access medical images of patients who potentially have lung cancer. In downloading the images, data packets 312 may be utilized for communicating the data as understood in the art. Furthermore, the medical image reading professionals may communicate from the computing devices 308 to the server 302 diagnoses of medical conditions of patients. The server 302 may be configured to communicate with an auditor 314 that may perform the function of independently evaluating medical image reading professionals to verify correctness of their work. Alternatively, the medical professional network manager may perform the task of auditing the correctness of diagnoses by the medical image reading professionals for reading medical images. In either case, as described with regard to FIG. 2, medical insurance claims, treatment reports, and random quality assurance medical image readings may be utilized to determine the accuracy of diagnoses made by medical image reading professionals. Information generated by the auditor 314 or medical professional network manager may include scores, grades, or other metric to provide an overall score for a medical image reading professional. In one embodiment, a score may be a result of an objective analysis, subjective of analysis, or combination thereof. If a subjective analysis is performed, the analysis may take into account any mitigating circumstances by which the medical image reading professional made his or her diagnosis of the medical images. Mitigating circumstances may include a variety of situations, including poor imaging or otherwise.

Figure 4:
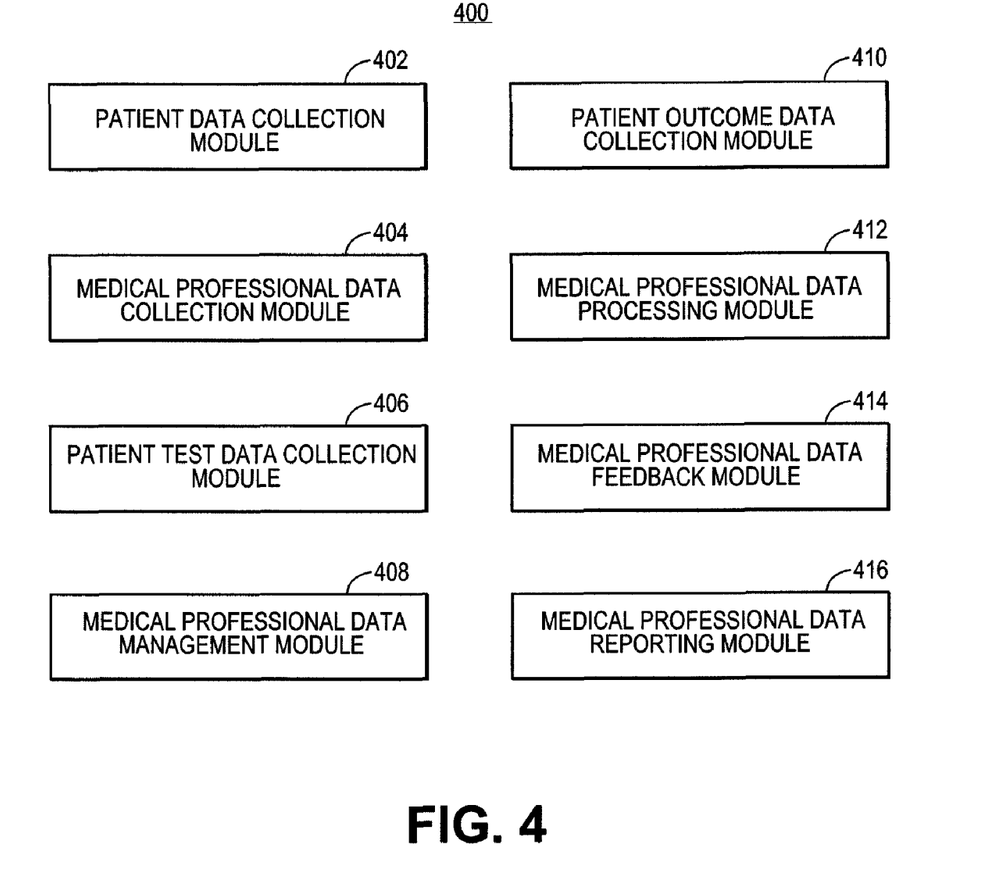
FIG. 4 is a block diagram of an exemplary software modules that may be utilized in performing data collection, processing, and reporting of medical professionals for determination of proficiency of medical professionals.

FIG. 4 is a block diagram of exemplary software modules 400 that may be utilized in performing data collection, processing, and reporting of medical professionals for determination of proficiency of medical professionals. The modules 400 are configured to perform a variety of functions used for collecting data associated with performing feedback of information that may be helpful in determining proficiency of a medical image reading professional in reading and diagnosing medical images of patients. Proficiency or skill of a medical image reading professional may be determined by the accuracy of his or her diagnosing medical conditions of patients.

The modules 400 may include a patient data collection module 402. The patient data collection module 402 may be utilized to collect patient data, as provided in FIG. 1. In collecting the patient data, the patient data collection module 402 may query a data repository to access the patient data. Alternatively, the patient data collection module 402 may provide for a user to enter patient data via a graphical user interface (GUI), such as a website, intranet site, or local GUI. Still yet, the data collection module 402 may be configured to receive patient data via text or other data files in an individual or batch file manner. After collecting the patient data, the patient data collection module 402 may be configured to store the patient data in a data repository, such as one of the data repositories 306a of FIG. 3.

A medical professional data collection module 404 may be configured in the same or similar manner as the patient data collection module 402. The medical professional data collection module 404 may collect or store medical professional data, as provided in FIG. 1, in a data repository.

A patient test data collection module 406 may be configured in the same or similar manner as the patient data collection module 402. The patient test data collection module 406 may collect or store patient test data, such as medical images, equipment type, etc., as provided in FIG. 1, in a data repository.

A medical professional data management module 408 may be configured to manage the data repositories in which the patient data, medical professional data, and patient test data are stored. Management of the data may include updating, backing up, deleting, editing, restructuring or performing any other data management function as understood in the art. Furthermore, because storage of patient data is generally governed by the Health Insurance Portability and Accountability Act (HIPAA), the medical professional data management module 408 is to be secure in limiting access to the data by being compliant with HIPAA standards.

A patient outcome data collection module 410 may be configured in the same or similar manner as the patient data collection module 402. However, because patient outcome data could involve one or more different groups or companies who collect the patient outcome data from medical insurance claims and treatment reports, the patient outcome collection module 410 may be configured to access or receive the patient outcome data using one or more interfaces depending on the type of patient outcome data being collected. For example, a patient having a lung condition may have significantly different patient outcome parameters than a patient who has a torn ligament in his or her knee. It should be understood that the patient outcome collection module 410 may include rules or intelligence to perform error checking of medical treatments selected by medical professionals based on a diagnosis made by a medical image reading professional, thereby reducing risks to patients.

A medical professional data processing module 412 may be configured to access patient outcome data, which may include the medical insurance claim analysis data, treatment report analysis data, and random quality assurance medical image read data, to determine accuracy of a medical image reading professional. In determining accuracy of a medical image reading professional, the medical professional data processing module 412 may determine whether a patient has had one or more medical procedures (e.g., biopsies) and results of each medical procedure may be used to determine whether a misdiagnosis occurred by the medical image reading professional who diagnosed the patient. In one embodiment, the medical professional data processing module 412 may be configured to group treatment data associated with an episode of care, where the treatment data may include all diagnoses and treatment information associated with treating a particular medical condition. The medical professional data processing module 412 may include a treatment grouper submodule (not shown) in performing the treatment grouping operation.

A medical professional data feedback module 414 may be configured to utilized the accuracy of the medical image reading professional determined by the medical professional data processing module 412 and feed back the accuracy information to enable a medical image reading professional network manager to determine whether the medical image reading professionals in the network are maintaining a certain level of accuracy or proficiency relative to specific medical conditions, anatomical regions, and/or imaging modalities to remain active in the network. Feeding back the accuracy of each medical image reading professional may include performing a number of functions, including storing each accuracy reading (i.e., each diagnostic accuracy determination) in a data repository, performing statistical computations with each accuracy reading, notifying the medical image reading professional network manager of a current level of accuracy, and/or performing any other functional operation to maintain up-to-date accuracy information of each medical image reading professional with respect to patient outcome of respective patients.

A medical professional data reporting module 416 may be configured to utilize the medical professional data determined by the medical professional data processing module 412 and generate one or more reports that present accuracy information of one or more medical image reading professionals. Tables, graphs, or any other alphanumeric or graphical representation may be utilized to show trend lines, cumulative data, historical data, or any other data indicative of the accuracy for medical image reading professionals to diagnose medical conditions of patients. In one embodiment, the medical professional data reporting module 416 may organize each medical image reading professional in a medical image reading professional network in a particular expertise according to anatomical region, medical condition, or modality with respect to each anatomical region. In creating a report, the medical professional data reporting module 416 may utilize the statistics calculated by the medical professional data processing module 412, medical professional data feedback module 414, or generated by the medical professional data reporting module 416 itself. Ultimately, the accuracy information generated by the medical professional data reporting module 416 may be used to identify the best medical image readers so that additional medical images may be concentrated to the best medical image readers, thereby improving accuracy and reducing costs for the overall healthcare system.

Figure 5:
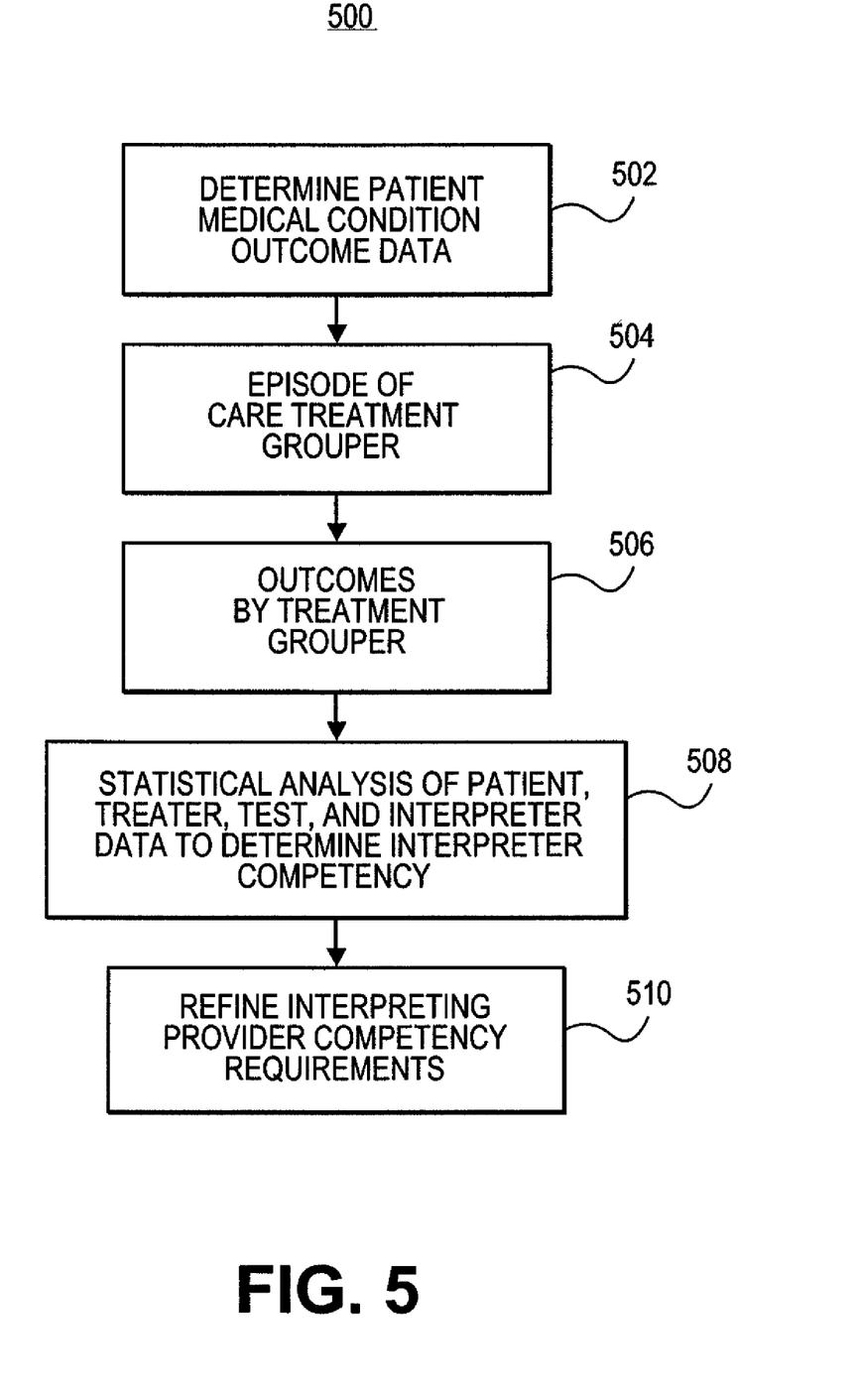
FIG. 5 is a flow diagram of an exemplary process for collecting medical condition outcome data of patients, processing the medical condition outcome data, and refining competency requirements for medical professionals.

FIG. 5 is a flow diagram of an exemplary process 500 for collecting medical condition outcome data of patients, processing the medical condition outcome data, and refining competency requirements for medical professionals. In one embodiment, the process 500 is performed, at least in part, by the server 302 of FIG. 3. The process 500 starts at step 502, where patient medical condition outcome data is determined. At step 504, an episode of care treatment grouper module may be configured to group all diagnoses and medical treatment data associated with an episode of care for a medical condition. In grouping the treatment data, start and stop codes or indicators may be utilized to indicate an initiate and close an episode of care.

At step 506, outcomes may be generated by the treatment grouper. An outcome of a patient is indicative of an actual medical condition of the patient. The outcomes may also include statistical information or any other information associated with treatment of the patient and diagnosis by medical image reading professionals and treating medical professionals of the patient. At step 508, a statistical analysis of the patient, treating physician, and medical image reading professional or interpreter data may be utilized to determine competency of the medical image reading professional. The statistical analysis may include the use of any mathematical equation to generate one or more values, such as a grade or rating, to enable comparison of each medical image reading professional as to their respective competency.

At step 510, interpreting provider or medical image reading professional requirements may be refined. The requirements refer to a level of accuracy that each medical image reading professional may be allowed to remain in a network or pool of medical image reading professionals. The network may have specializations of medical image reading professionals, such that medical image reading professionals of one specialization may have different requirements than other specializations due to difficulty, level of effect on patients for misdiagnoses, or any other parameter. For example, a medical image reading professional expert for reading shoulder images may have a lower threshold of accuracy than an expert for reading brains for cancer. Over time, refinement of the requirements may include determining a minimum level of accuracy for each expertise to minimize harmful effects to patient outcomes and adjusting the minimum level of accuracy for each respective expertise.

Medical image reading professionals who are highly skilled may have historical attributes to their careers or personal lives that caused them to become highly skilled. Being highly skilled may mean that a medical image reading professional is in the top 3% or 5% of all medical image reading professionals who read medical images of the same modality, anatomical regions, and/or medical conditions. The historical attributes of a medical image reading professional may include particular schools, professors, supervisors, mentors, curriculum, grade point averages, sports participation, or any other attribute, either directly or indirectly related to medical training, physical characteristics (e.g., eyesight), or mental skill (e.g., logical reasoning, obsessive compulsiveness, or "A" type personality). The historical attributes may be collected and stored in one or more databases. A searching or mining software algorithm executed on a computer may be configured to access and search the database(s) to identify historical data of highly skilled medical image reading professionals that are related to or match experts for reading particular modalities, anatomical regions, and/or conditions, thereby enabling a medical image reading professional network manager to better "scout" medical image reading professionals who are or have the potential to become highly skilled.

Figure 6:
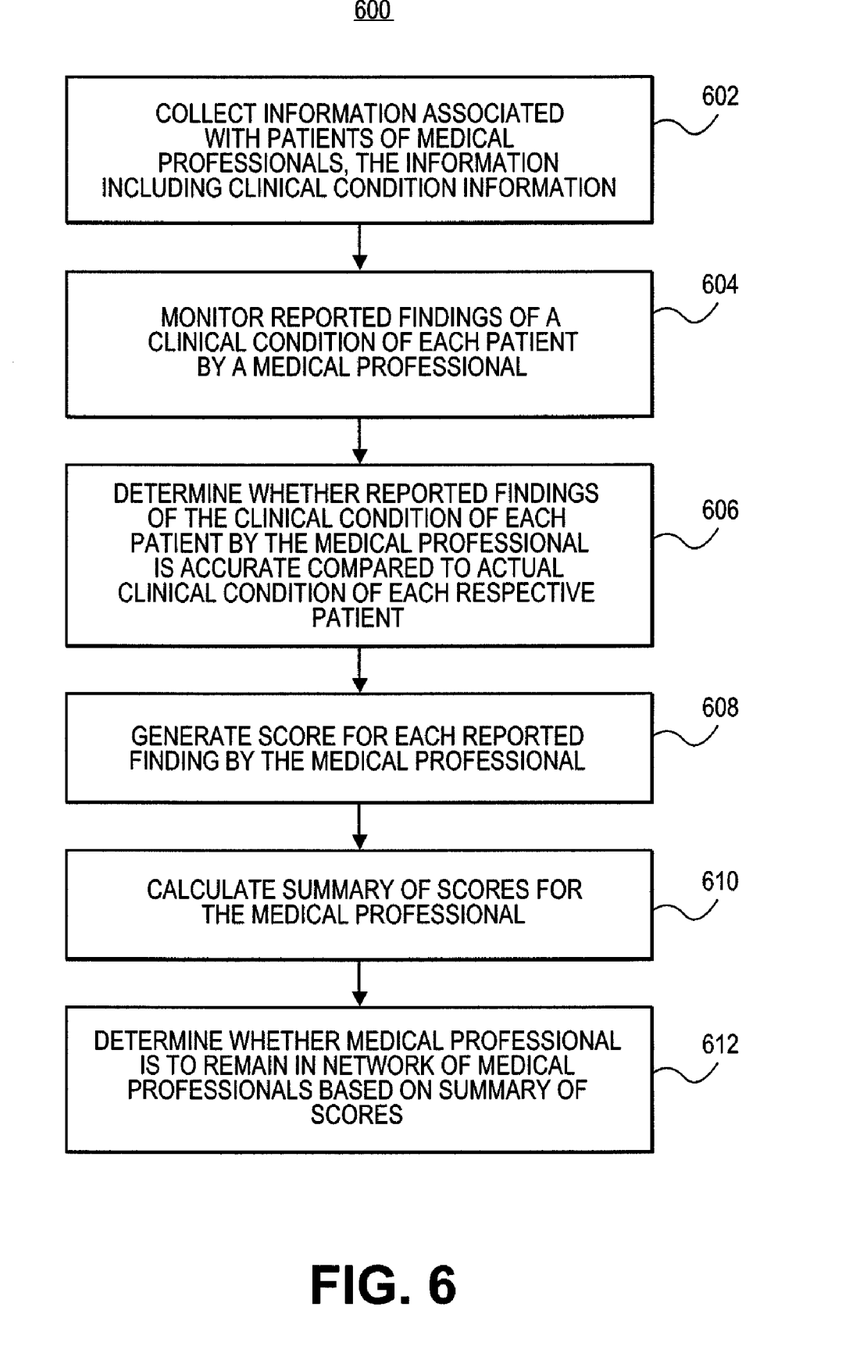
FIG. 6 is a flow diagram of an exemplary process for managing a network of medical professionals.

FIG. 6 is a flow diagram of an exemplary process 600 for managing a network of medical professionals. The process 600 includes collecting information associated with patients of medical professionals in a network of medical professionals. The patient information may include clinical condition information. Reported findings of a clinical condition of each patient by a medical professional may be monitored at step 604. In one embodiment, the medical professional is a medical image reading professional. At step 606, a determination may be made as to whether the reported findings of the clinical condition of each patient by the medical professional is accurate compared to actual clinical condition of each respective patient. A score for each reported finding by the medical professional may be generated at step 608, where the score may be indicative of accuracy of each reported finding as compared to the actual clinical condition of the patient. A summary score of the scores for the medical professional may be calculated at step 610 and, based on the summary score of the medical professional, a determination may be made as to whether the medical professional is to remain in the network of medical professionals at step 612.

In determining a score, a predetermined score for each of an accurate, false positive, false negative, or false equivocal reported finding being correct or incorrect may be made. Furthermore, a determination of an equivocal ratio by the medical professional may be made to determine whether the medical professional has a high ratio, which could indicate that the medical professional lacks ability to diagnose certain clinical conditions (i.e., medical conditions). In addition, a determination may be made as to a total number of reported findings by the medical professional may be made over a given time period, such as a month, to determine proficiency and efficiency of the medical professional. In collecting the information associated with the patients, sets of medical images associated with each patient may be collected. The reported findings may be monitored to determine whether the medical professional accurately diagnoses the clinical condition of each patient in reading respective sets of medical images. In generating the summary score, an average of the scores may be generated. Monitoring reported findings may include analyzing medical insurance claims, treatment reports, and/or random quality assurance medical image readings. The analysis may be objective or subjective. In one embodiment, different weightings may be applied to different clinical conditions so that more difficult clinical conditions are weighted with a higher value to compensate the medical image reading professional who is diagnosing clinical conditions that are more difficult to accurately diagnose. A report including medical image reading professionals who specialize in reading the particular anatomical region and respective summary scores may be generated, where the medical image reading professional and associated summary score may be included in the report.

Figure 7:
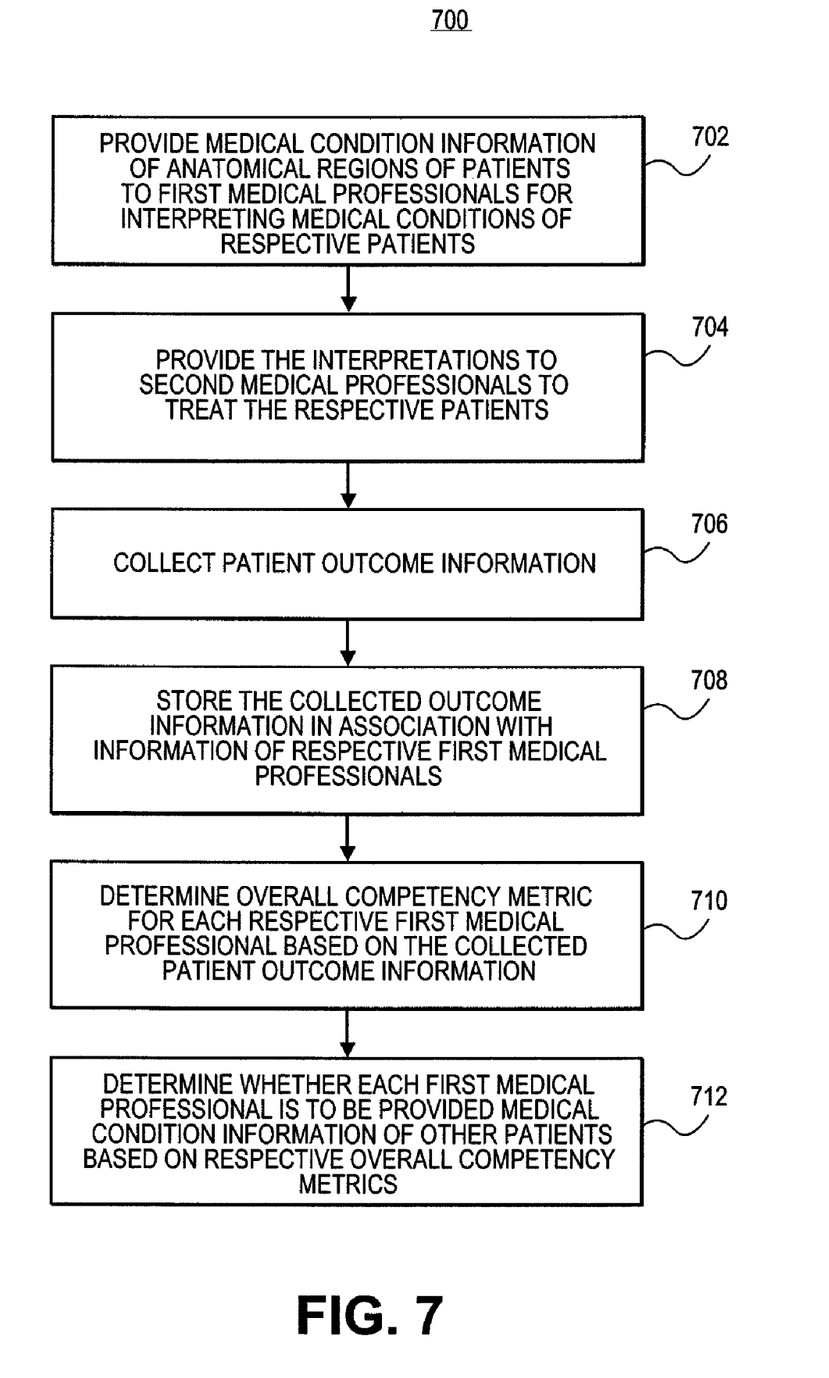
FIG. 7 is a flow diagram of an exemplary process for improving medical care.

FIG. 7 is a flow diagram of an exemplary process 700 for improving medical care. The process 700 may include providing medical condition information of anatomical regions of patients to first medical professionals for interpreting the medical condition information to describe medical conditions of the respective patients at step 702. The first medical professionals may be medical image reading professionals. The medical condition information may include medical images, such as radiological images, and the descriptions of medical conditions may be diagnoses of the medical images. At step 704, the interpretations of the medical condition information may be provided to second medical professionals to treat the respective patients for medical conditions described in the interpretations by the first medical professionals. The second medical professionals may be treating physicians who use the described medical conditions for developing treatment plans for respective patients. Patient outcome information associated with outcome of the patients treated for the medical conditions described in the interpretations may be collected at step 706. At step 708, the collected patient outcome information may be stored in association with information of respective first medical professionals who interpreted medical condition information of the respective patients. At step 710, a determination may be made of an overall competency metric for each first medical professional indicative of performance of each respective first medical professional based on the collected patient outcome information. In one embodiment, the overall competency metric may be an average competency metric value of the assigned competency metric values assigned to each interpretation for each respective first medical professional. At step 712, a determination as to whether each first medical professional is to be provided medical condition information of other patients based on respective overall competency metrics may be made.

The previous detailed description of a small number of embodiments for implementing the invention is not intended to be limiting in scope. One of skill in this art will immediately envisage the methods and variations used to implement this invention in other areas than those described in detail. The following claims set forth a number of the embodiments of the invention disclosed with greater particularity.

What is claimed:

1. A method for managing a network of medical image reading professionals, said method comprising:
   collecting, by a computing system, information associated with patients of medical image reading professionals in a network of medical image reading professionals, the patient information including clinical condition information, the collecting of information associated with patients including collecting sets of medical images;

monitoring reported findings of a clinical condition of each patient by a medical image reading professional including monitoring the diagnosis of each patient by the medical image reading professional in reading the sets of medical images, the monitoring of reported findings including at least one of analyzing medical insurance claims, analyzing treatment reports, and analyzing random quality assurance medical image readings;

determining, by the computing system, whether the reported findings of the clinical condition of each patient by the medical image reading professional is accurate compared to actual clinical condition of each respective patient;

generating a score for each reported finding by the medical image reading professional, the score being indicative of accuracy of each reported finding as compared to the actual clinical condition of the patient, the generating of a score including applying a predetermined score for each of an accurate, false positive, false negative, or false equivocal reported finding being correct or incorrect;

calculating a summary score of the scores for the medical image reading professional; and based on the summary score of the medical image reading professional, determining whether the medical image reading professional is to remain in the network of medical image reading professionals, and, if not, removing the medical image reading professional from the network of medical image reading professionals; and sending more medical images to medical image reading professionals with higher scores than medical image reading professionals with lower scores.

2. The method according to claim 1, further comprising determining an equivocal ratio for the medical image reading professional.

3. The method according to claim 1, further comprising determining a total number of reported findings by the medical image reading professional over a given time period.

4. The method according to claim 1, wherein generating a summary score includes generating an average score.

5. The method according to claim 1, wherein monitoring reported findings by a medical image reading professional includes monitoring reported findings by a medical image reading professional who specializes in reading medical images of a particular anatomical region.

6. The method according to claim 5, further comprising generating a report that includes (i) a plurality of medical image reading professionals who specialize in reading medical images of the particular anatomical region and (ii) respective summary scores, the medical image reading professional and associated summary score being included in the report.

* * * * *